United States Patent [19]
Bhattacharya et al.

[11] Patent Number: 5,399,670
[45] Date of Patent: Mar. 21, 1995

[54] SOLUBILIZATION AND STABILIZATION OF FACTOR VIII COMPLEX

[75] Inventors: Prabir Bhattacharya, Walnut; Toshiharu Motokubota, Arcadia, both of Calif.

[73] Assignee: Alpha Therapeutic Corporation, Los Angeles, Calif.

[21] Appl. No.: 54,903

[22] Filed: Apr. 29, 1993

Related U.S. Application Data

[63] Continuation-in-part of Ser. No. 876,190, Apr. 30, 1992, abandoned.

[51] Int. Cl.$^6$ .................... A61K 37/02; A61K 37/06; C07K 13/00; C07K 3/20
[52] U.S. Cl. .................... 530/383; 530/417; 530/427
[58] Field of Search .................... 530/383, 417, 427; 514/12, 21

[56] References Cited

U.S. PATENT DOCUMENTS

| | | | |
|---|---|---|---|
| 4,623,717 | 11/1986 | Fernandes | 514/21 |
| 4,650,678 | 3/1987 | Fuhge et al. | 424/101 |
| 4,650,858 | 3/1987 | Rasmussen et al. | 530/383 |
| 4,758,657 | 6/1988 | Farb et al. | 530/383 |
| 5,110,907 | 5/1992 | Kosow et al. | 530/413 |

FOREIGN PATENT DOCUMENTS 61-022022 1/1986 Japan.

*Primary Examiner*—Howard E. Schain
*Assistant Examiner*—Lynn Touzeau
*Attorney, Agent, or Firm*—Christie, Parker & Hale

[57] ABSTRACT

A process for facilitating the reconstitution of lyophilized Factor VIII complex compositions, and compositions of Factor VIII complex, which are readily reconstituted. The process of the present invention comprises providing a purified Factor VIII complex preparations; adding a stabilization agent comprising arginine; lyophilizing the stabilization agent-Factor VIII complex solutions; and reconstituting the lyophilized stabilization agent-Factor VIII complex by contacting it with solvent for less than one minute.

49 Claims, No Drawings

SOLUBILIZATION AND STABILIZATION OF FACTOR VIII COMPLEX

RELATED APPLICATION

This application is a continuation-in-part of U.S. application Ser. No. 07/876,190, filed Apr. 30, 1992, now abandoned, which is incorporated herein by reference.

FIELD OF THE INVENTION

This invention relates to an improved process for solubilizing lyophilized antihemophilic factor (Factor VIII complex) preparations.

BACKGROUND OF THE INVENTION

Coagulation of blood is a complex process requiring the sequential interaction of a large number of components, nearly all of which are proteins. These components include fibrinogen and Factors II, V, VII, VIII, IX, X, XI, and XII. A lack of any of these components, or a nonfunctional component, can lead to an inability of the blood to clot when required, with resultant excessive and life-threatening blood loss to the patient.

Factor VIII (antihemophilic factor) is present at deficient levels, or is absent, in certain individuals. For example, persons who have a deficiency (or absence) of Factor VIII, i.e., persons suffering from hemophilia A, have blood which either fails to clot or clots only after longer periods of time than the time required for clotting in a person who has a normal level of Factor VIII.

Factor VIII is present in plasma as a high-molecular-weight complex (Factor VIII complex), which includes Factor VIII:C and von Willebrand factor (Factor VIII:R or vWf). Factor VIII:C promotes blood coagulation. Factor VIII:R promotes aggregation of platelets and, when incorporated into the Factor VIII complex, acts as a stabilizer for Factor VIII:C.

Purification of the Factor VIII complex has resulted in Factor VIII preparations which have a purity level of about 90% or greater, and which are sufficiently stable for storage for long periods of time in a lyophilized form. As used herein, purity means the amount of the specified protein as a percentage of the total amount of protein in a sample. However, highly-purified, lyophilized Factor VIII complex compositions, i.e., compositions with a high Factor VIII:C specific-activity, are difficult to reconstitute in aqueous solutions such as those required for use in intravenous injection. The purified solutions require contact with solvents for extended periods of time (about 5-6 min.) before they are resolubilized, and often result in reconstituted solutions which have poor clarity, thus wasting valuable time of hospital employees.

In addition, the reconstituted Factor VIII complex compositions have a limited life, requiring that the reconstituted compositions be discarded after a short period of time. This presents difficulties in the treatment of patients who require injections of Factor VIII complex to maintain blood-clotting ability. Typically, such patients are injected with a dose of about 50 units of Factor VIII:C/kg of body weight about every one to two weeks, although injection schedules vary from person to person depending on the severity of the individual's hemophilia.

In U.S. Pat. No. 4,650,858 to Rasmussen et al., Factor VIII is purified using a two-step PEG precipitation purification scheme, wherein an amino acid or other "salting-in" agent is added to the second PEG precipitation to salt-in contaminants and to give a "sharper" purification of the Factor VIII. The salting-in agent used in this method would be substantially removed from the final Factor VIII preparation as a result of the subsequent precipitation of the Factor VIII by PEG. The specific-activity of the Factor VIII is limited to only 3.85 to 50 units/mg.

There is a need to provide a lyophilized Factor VIII complex composition which has enhanced solubility in aqueous solutions. It is also desirable that the reconstituted Factor VIII complex is stable at room temperature, so that, once a solution is reconstituted, it can be stored for extended periods of time prior to use.

SUMMARY OF THE INVENTION

A process for producing a lyophilized Factor VIII complex composition which, when reconstituted, exhibits enhanced solubility, is described. An aqueous solution comprising a Factor VIII complex preparation incorporating at least 50 units of Factor VIII:C activity per milligram of total protein in the preparation is mixed with a solubilizing agent, comprising arginine, to thereby form a Factor VIII/arginine solution. The Factor VIII/arginine solution is lyophilized to thereby provide a lyophilized Factor VIII composition with enhanced solubility.

Histidine and human serum albumin may also be added to the solubilizing agent. In a preferred embodiment arginine is present at a concentration of about 0.05M to about 0.5M, and most preferably from about 0.1 to about 0.2M, prior to lyophilization. Histidine, when added, is present at a concentration of about 0.025M and the human serum albumin, when added, is present at a concentration of about 0.05% to about 3%, preferably about 0.5%, prior to lyophilization.

In a preferred embodiment, the Factor VIII complex preparation has a specific-activity of about 50 to about 500 units/mg, and the lyophilized Factor VIII complex composition is reconstituted with water at room temperature.

DETAILED DESCRIPTION

The process of the present invention provides a simple and efficient method for the preparation of solutions of high specific-activity Factor VIII complex at high concentrations from lyophilized Factor VIII complex compositions. Concentrations of greater than from about 50 units of Factor VIII:C activity/ml are contemplated by the present invention. The phrase "high specific-activity" as used herein means a Factor VIII complex preparation having greater than about 50 units of Factor VIII:C activity/mg of protein. While the reconstitution method of the present invention is suitable for use with high concentrations and high specific-activity Factor VIII complex preparations, it is also suitable for use with lower concentrations and lower specific-activity Factor VIII complex preparations.

The starting material from which the high specific-activity Factor VIII complex product provided in accordance with the present invention is derived, may be cryoprecipitate or other blood plasma-derived fractions, or it may be derived by recombinant-DNA or transgenic techniques.

Any purification procedure which results in a Factor VIII complex having a high Factor VIII:C specific-activity is suitable for use in accordance with the practice of the present invention. In one exemplary embodiment, Factor VIII complex is purified from cryoprecipitate using affinity chromatography and precipitation techniques.

A key step of the process of the present invention is that the high specific-activity Factor VIII complex, from whatever source, is lyophilized in the presence of a sufficient amount of arginine to enhance its solubility. As used herein enhanced solubility means the solubility of the Factor VIII complex which has been lyophilized in the presence of the solubilizing agent of the present invention compared to Factor VIII complex which has been lyophilized in the absence of the solubilizing agent of the present invention. Other amino acids and/or proteins may be present in addition to arginine. Preferably, the high specific-activity Factor VIII complex is lyophilized in an aqueous solution which includes a solubilizing agent, arginine. The solubilizing agent may further comprise histidine and human serum albumin. The Factor VIII complex with enhanced solubility is prepared from an aqueous solution comprising from about 0.05M to about 0.5M arginine and about 0.1 mg to about 5 mg/ml of Factor VIII complex. When added, histidine and human serum albumin are present at a concentration of about 0.025M and about 0.05% (wt/vol) to about 3% (wt/vol), respectively. As used herein % refers to % weight per volume (wt/vol), unless otherwise specified. Preferably, the aqueous solution from which the Factor VIII is lyophilized comprises about 0.1 to about 0.2M arginine, about 0.025M histidine and about 0.5% (wt/vol) human serum albumin. The histidine acts as a buffer. While other buffers may be used, histidine is preferred, since it does not lead to precipitation of the Factor VIII complex or otherwise adversely affect its solubility.

It was discovered that, surprisingly, the arginine acts as a solubilizing agent and aids in the rapid reconstitution of the lyophilized Factor VIII complex. The human serum albumin acts as a bulking agent and aids in the long-term stability of the lyophilized Factor VIII complex, once it has been reconstituted.

Preferably, the Factor VIII complex/solubilization agent solution is aliquoted into separate vials, each of which is filled with an amount of Factor VIII complex sufficient for at least a single dose of Factor VIII complex. The Factor VIII complex composition is then lyophilized to provide a lyophilized Factor VIII composition of enhanced solubility. The lyophilized composition may be stored at about 4° C. until required for use.

When required for use, the lyophilized Factor VIII complex composition, incorporating the solubilization agent, may be readily reconstituted in water or other suitable media. The lyophilized Factor VIII complex reconstitutes in water, in less than 1 min., to provide a solution which has a high degree of clarity and which is stable for extended periods of time at room temperature.

Preparation of Factor VIII Complex for Facilitated Reconstitution

To facilitate the resolubilization of the lyophilized Factor VIII complex, an aqueous solution comprising about 0.1 to about 5 mg/ml of a high specific activity Factor VIII complex preparation, i.e. a Factor VIII complex having an activity of greater than 50 units/mg of Factor VIII:C activity/mg of protein, and arginine is prepared. Histidine and human serum albumin may also be added to the solution. Preferably, the final concentration of the solubilization agent components is about 0.05M to about 0.5M arginine, about 0.025M histidine, and from about 0.05% (wt/vol) to about 3% (wt/vol) human serum albumin. Most preferably, the final concentration of the solubilization agent components is about 0.1M to about 0.2M arginine, about 0.025M histidine, and about 0.5% (wt/vol) human serum albumin. The solution is then lyophilized and stored at 4° C. until required for use. When required for use, the lyophilized Factor VIII complex is dissolved in distilled water or a suitable buffer solution.

The present invention could be practiced with any Factor VIII complex purification procedure which results in the preparation of Factor VIII complex of a high specific-activity.

EXAMPLE 1

Preparation of Purified Factor VIII Complex 9,030 kg of plasma were cryoprecipitated by freezing the plasma at a temperature of about −20° C. and is subsequently thawed at 0° C. to 5° C. The 107 kg of cryoprecipitate which forms during the thawing process was collected and dissolved in 320 liters (l) of distilled water containing about 120 units of heparin per ml of water. The heparin solution was mixed at a temperature of 30° C. until the cryoprecipitate was completely dissolved (approximately 10 min.), to provide a cryoprecipitate/heparin solution. After the cryoprecipitate was dissolved, the pH of the cryoprecipitate/heparin solution was adjusted to about 7, using 0.1M HCl, and the solution was stirred for an additional 20 to 30 min.

An aqueous PEG solution comprising 31.5% (wt/vol) PEG, 0.22% (wt/vol) sodium citrate dihydrate, and 0.08% (wt/vol) citric acid monohydrate, at a pH of 6.2, was then added to the cryoprecipitate/heparin solution, to give a final concentration of 3.5% (wt/vol) PEG. The pH of the PEG/cryoprecipitate/heparin solution was adjusted to 6.3 with dilute acetic acid. The pH-adjusted solution was mixed for approximately 15 min., at a temperature of 27° C. The addition of PEG resulted in precipitation of various contaminating proteins from the Factor VIII complex, which remained in solution.

The PEG precipitate was separated from the Factor VIII complex-containing supernatant solution by centrifugation. The PEG supernatant, i.e., the Factor VIII complex containing impure protein fraction, was recovered. The supernatant was then treated to inactivate viruses which may be present in the blood products, by the addition of a solution containing 0.3% (wt/vol) tri-n-butylphosphate and 1% (wt/vol) TWEEN-80 and incubating at 25° C. for 6 hrs.

The viral-inactivated supernatant solution, i.e., the viral-inactivated Factor VIII complex containing impure protein fraction, was clarified by filtration and then recovered for further purification of Factor VIII complex by affinity chromatography on a heparin-coupled chromatographic medium.

The Factor VIII complex-containing solution was applied to a 200 liter (l) heparin-coupled chromatographic medium packed into the column. The column effluent was collected, and the column was washed with 1700 l of 0.025M histidine, pH 6.8, containing 0.10M NaCl. Elution of Factor VIII complex was achieved with 600 l of 0.1M $CaCl_2$ and 0.025M histidine, pH 6.8.

The eluate from a heparin column (the column eluate) was concentrated 15-fold using a CENTRASETTE, Omega 100K cassette. The concentrated solution, i.e., the eluate concentrate, was then brought to 2M glycine and 1.2M NaCl and mixed at 25° C. for 2 hours. The precipitate which formed was collected by centrifugation and washed with a wash solution comprising 0.025M histidine, pH 6.8, 2M glycine, and 1.3M NaCl. The washed precipitate was collected by filtration.

To perform an assay on the purified Factor VIII complex, a sample of the washed precipitate was dissolved in a buffer comprising 0,025M histidine, 0.1M arginine, pH 7.0 to 7.6, to a concentration of 0.5 mg of Factor VIII complex/ml of buffer.

The resultant solution and aliquots taken from various stages during the purification, were then assayed for Factor VIII:C blood-clotting activity using a COAG-A-MATE XC clotting machine. The results are summarized in Table I.

TABLE I

| Sample | Units[1] × $10^{-3}$ | Units[1]/kg Plasma | Specific-Activity units/mg |
|---|---|---|---|
| Plasma | 9,030 | 1,000 | 0.01 |
| Cryoprecipitate | 3,540 | 392 | 0.7 |
| PEG-supernatant | 3,645 | 404 | 1.5 |
| Column eluate | 2,640 | 292 | — |
| Eluate Conc. | 1,540 | 171 | 14.5 |
| Glycine/NaCl precipitate | 782 | 87 | 99.1 |

[1]Units of Factor VIII:C specific-activity.

The resultant purified Factor VIII complex solution was further analyzed to evaluate the contaminating proteins present. The results are summarized in Table II.

TABLE II

| Specific-activity (Factor VIII:C units/mg) | 99.1 |
|---|---|
| Fibronectin (μg/unit*) | 1.5 |
| Fibrinogen (μg/unit) | <0.8 |
| IgG (μg/unit) | <0.1 |
| IgM (μg/unit) | ≦0.1 |
| HSA (μg/unit) | <0.1 |

*per unit of Factor VIII:C

EXAMPLE 2

Lyophilization and Reconstitution of Purified Factor VIII Complex

Separate samples of a washed precipitate of Factor VIII complex, prepared as described in Example 1, were dissolved in solutions, incorporating a variety of constituents, to provide a concentration of 3 mg of Factor VIII complex/mi. The solutions were then lyophilized and the lyophilized Factor VIII complex was reconstituted with distilled water at room temperature with gentle agitation. The samples were observed, and the time required for the Factor VIII complex to dissolve was noted, as was the general appearance of the reconstituted Factor VIII. The constituents of the solutions used to dissolve the washed Factor VIII complex precipitate are summarized in Table III, and the results are summarized in Table IV.

TABLE III

| Solution Number | Constituents |
|---|---|
| 1 | 0.025 M histidine, 3 mg/ml Factor VIII complex |
| 2 | 0.1 M histidine, 3 mg/ml Factor VIII complex |
| 3 | 0.1 M glycine, 0.025 M histidine, 3 mg/ml Factor VIII complex |
| 4 | 0.28 M glycine, 0.025 M histidine, 3 mg/ml Factor VIII complex |
| 5 | 0.28 M glycine, 0.025 M histidine, 3% (wt/vol) dextrose, 3 mg/ml Factor VIII complex |
| 6 | 0.1 M lysine, 0.025 M histidine, 3 mg/ml Factor VIII complex |
| 7 | 0.28 M alanine, 0.025 M histidine, 3 mg/ml Factor VIII complex |
| 8 | 0.1 M arginine, 0.025 M histidine, 3 mg/ml Factor VIII complex |
| 9 | 0.1 M arginine, 0.025 M histidine, 0.5% (wt/vol) human serum albumin, 3 mg/ml Factor VIII complex |
| 10 | 0.28 M arginine, 0.025 M histidine, 3 mg/ml Factor VIII complex |
| 11 | 0.28 M arginine, 0.025 M histidine, 0.5% (wt/vol) human serum albumin, 3 mg/ml Factor VIII complex |

TABLE IV

| No. | Constituents in Factor VIII Solution | Reconstitution Time (sec.) | Appearance |
|---|---|---|---|
| 1 | 0.025 M histidine | 170 | tiny protein strings |
| 2 | 0.1 M histidine | 240 | hazy |
| 3 | 0.1 M glycine, 0.025 M histidine | 480 | hazy |
| 4 | 0.28 M glycine, 0.025 M histidine | 720 | not clear |
| 5 | 0.28 M glycine, 0.025 M histidine, 3% (wt/vol) dextrose | 110 | not clear |
| 6 | 0.1 M lysine, 0.025 M histidine | 360 | not clear |
| 7 | 0.28 M alanine, 0.025 M histidine | 480 | hazy |
| 8 | 0.1 M arginine, 0.025 M histidine | 50 | clear |
| 9 | 0.1 M arginine, 0.025 M histidine, 0.5% (wt/vol) human serum albumin | 15 | clear |
| 10 | 0.28 M arginine, 0.025 M histidine | 50 | clear |
| 11 | 0.28 M arginine, 0.025 M histidine, 0.5% (wt/vol) human serum albumin | 40 | clear |

The results indicate that arginine is effective as an agent to enhance the resolubilization of lyophilized Factor VIII complex as can be seen from a comparison of the results in Examples 3, 4 and 7 with Example 8. In these Examples an amino acid is combined with a buffer, histidine. Only the combinations which incorporated arginine were found to be effective as reconstitution agents. Histidine alone, see Examples 1 and 2, was not and 2, was not an effective reconstitution agent. The combinations 0.1M arginine, 0,025M histidine; 0.1M arginine, 0.025M histidine, 0.5% (wt/vol) human serum albumin; 0.28M arginine, 0,025M histidine; and 0.28M arginine, 0.025M histidine, and 0.5% (wt/vol) human serum albumin are effective as agents to enhance the resolubilization of lyophilized Factor VIII complex.

EXAMPLE 3

Stability of Reconstituted Purified Factor VIII Complex

A washed precipitate of Factor VIII complex, prepared as described in Example 1, was dissolved to a concentration of 3 mg of Factor VIII complex in 0.025M histidine. The sample was divided into two portions. One portion was brought to 0.1M arginine and 0.5% (wt/vol) human serum albumin by the addition of arginine and human serum albumin. The other portion was brought to 0.1M glycine and 0.5% (wt/vol) human serum albumin by the addition of glycine and human serum albumin. The samples were then lyophilized. Each of the lyophilized preparations was then reconstituted in water, to give a Factor VIII complex concentration of 3 mg/ml, and the samples were incubated at room temperature for up to 22 days. Each of the reconstituted Factor VIII complex solutions was sampled periodically and assayed for Factor VIII:C activity. The results are summarized in Table V.

TABLE V

| | % Specific-Activity Remaining When Incubated In: | |
|---|---|---|
| Day | 0.1 M Arg, 0.025 M His, 0.5% HSA | 0.1 M Gly, 0.025 M His, 0.5% HSA |
| 0 | 100 | 100 |
| 3 | 119 | 92 |
| 9 | 123 | 73 |
| 22 | 88 | 2 |

Arg = Arginine
His = Histidine
Gly = Glycine
HSA = Human Serum Albumin

The results indicate that a preparation containing 0.1M arginine, 0.025M histidine, and 0.5% (wt/vol) human serum albumin is effective in stabilizing Factor VIII complex when it is reconstituted in an aqueous solution and that 88% of the original, reconstituted activity of the Factor VIII complex was retained after 22 days at room temperature. Only 2% of the original, reconstituted activity of the Factor VIII complex was retained in samples that had glycine in place of arginine.

The above descriptions of exemplary embodiments of processes for facilitating the reconstitution of lyophilized Factor VIII complex compositions are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A process for producing a lyophilized Factor VIII complex composition which, when reconstituted, exhibits enhanced solubility, the process comprising:
   providing an aqueous solution comprising a Factor VIII complex preparation incorporating at least 50 units of Factor VIII:C activity per milligram of total protein in the preparation;
   adding a solubilizing agent comprising arginine to the aqueous solution to thereby form a Factor VIII/arginine solution; and
   lyophilizing the Factor VIII/arginine solution to thereby provide a lyophilized Factor VIII composition with enhanced solubility.

2. A process as recited in claim 1 wherein the solubilization agent further comprises histidine.

3. A process as recited in claim 1 wherein the solubilization agent further comprises human serum albumin.

4. A process as recited in claim 1 wherein the arginine is present at a concentration of about 0.05M to about 0.5M.

5. A process as recited in claim 1 wherein the arginine is present at a concentration of about 0.1M to about 0.2M.

6. A process as recited in claim 2 wherein the histidine is present at a concentration of about 0.025M.

7. A process as recited in claim 3 wherein the human serum albumin is present at a concentration of about 0.05% (wt/vol) to about 3% (wt/vol).

8. A process as recited in claim 3 wherein the human serum albumin is present at a concentration of about 0.5% (wt/vol).

9. A process for producing a reconstituted lyophilized Factor VIII complex composition by adding water to lyophilized Factor VIII complex composition.

10. A process as recited in claim 9 wherein the lyophilized Factor VIII complex composition is reconstituted, to form a reconstituted Factor VIII complex composition, at room temperature in less than one minute to provide a clear solution.

11. A process as recited in claim 10 wherein the reconstituted Factor VIII complex composition retains at least 80% of its original reconstituted specific-activity after the reconstituted Factor VIII complex is incubated for about 22 days at room temperature.

12. A process for facilitating the reconstitution of lyophilized Factor VIII complex compositions comprising:
   providing a purified Factor VIII complex preparation in aqueous solution;
   adding a solubilization agent comprising arginine to the Factor VIII complex solution;
   lyophilizing the solubilization agent-Factor VIII complex solution; and
   contacting the lyophilized solubilization agent-Factor VIII complex with water for less than one minute at room temperature to reconstitute the Factor VIII complex composition.

13. A process as recited in claim 12 wherein the solubilization agent further comprises histidine.

14. A process as recited in claim 12 wherein the solubilization agent further comprises human serum albumin.

15. A process as recited in claim 12 wherein the arginine is present at a concentration of about 0.05M to about 0.5M.

16. A process as recited in claim 12 wherein the arginine is present at a concentration of about 0.1M to about 0.2M.

17. A process as recited in claim 13 wherein the histidine is present at a concentration of about 0.025M.

18. A process as recited in claim 14 wherein the human serum albumin is present at a concentration of about 0.05% (wt/vol) to about 3% (wt/vol).

19. A process as recited in claim 14 wherein the human serum albumin is present at a concentration of about 0.5% (wt/vol).

20. A process as recited in claim 12 wherein the Factor VIII complex composition has a specific-activity of at least 50 units of Factor VIII activity per mg of total protein.

21. A process as recited in claim 12 wherein the reconstituted Factor VIII complex composition retains at least 80% of its original reconstituted specific-activity after the reconstituted Factor VIII complex is incubated for about 22 days at room temperature.

22. A process for enhancing the reconstitution of lyophilized Factor VIII complex compositions and the stability of reconstituted Factor VIII complex compositions, the process comprising:
providing a purified Factor VIII complex preparation;
adding a solubilization agent to the Factor VIII complex preparation wherein the solubilization agent comprises arginine, histidine and human serum albumin;
lyophilizing the solubilization agent-Factor VIII complex preparation; and
contacting the lyophilized solubilization agent-Factor VIII complex with water for less than one minute to reconstitute the Factor VIII complex composition.

23. A process as recited in claim 22 wherein the arginine is present at a concentration of about 0.05M to about 0.5M.

24. A process as recited in claim 22 wherein the arginine is present at a concentration of about 0.1M to about 0.2M.

25. A process as recited in claim 22 wherein the histidine is present at a concentration of about 0.025M.

26. A process as recited in claim 22 wherein the human serum albumin is present at a concentration of about 0.05% (wt/vol) to about 3% (wt/vol).

27. A process as recited in claim 22 wherein the human serum albumin is present at a concentration of about 0.5% (wt/vol).

28. A process as recited in claim 22 wherein the Factor VIII complex composition has a specific-activity of at least 50 units of Factor VIII:C activity per mg of total protein.

29. A process as recited in claim 22 wherein the reconstituted Factor VIII complex composition retains at least 80% of its original reconstituted specific-activity after the reconstituted Factor VIII complex is incubated for about 22 days at room temperature.

30. A lyophilized Factor VIII complex composition comprising purified Factor VIII complex and arginine, wherein the composition when contacted with water is reconstituted in less than a minute at room temperature.

31. A composition as recited in claim 30 wherein the composition further comprises histidine.

32. A composition as recited in claim 30 wherein the composition further comprises human serum albumin.

33. A composition as recited in claim 30 wherein the arginine is present, prior to lyophilization, at a concentration of about 0.05M to about 0.5M.

34. A composition as recited in claim 30 wherein the arginine is present, prior to lyophilization, at a concentration of about 0.1M to about 0.2M.

35. A composition as recited in claim 31 wherein the histidine is present, prior to lyophilization, at a concentration of about 0.025M.

36. A composition as recited in claim 32 wherein the human serum albumin is present, prior to lyophilization, at a concentration of about 0.05% (wt/vol) to about 3% (wt/vol).

37. A composition as recited in claim 32 wherein the human serum albumin is present, prior to lyophilization, at a concentration of about 0.5% (wt/vol).

38. A composition as recited in claim 30 wherein the Factor VIII complex preparation has a specific-activity of at least 50 units of Factor VIII:C activity per mg of total protein.

39. A process for improving the stability of an aqueous solution of purified Factor VIII complex, the process comprising:
providing a purified Factor VIII complex preparation;
adding a stabilization agent to the Factor VIII complex preparation wherein the stabilization agent comprises arginine;
lyophilizing the stabilization agent-Factor VIII complex preparation; and
reconstituting the lyophilized stabilization agent-Factor VIII complex in water.

40. A process as recited in claim 39 wherein the arginine is present at a concentration of about 0.05M to about 0.5M.

41. A process as recited in claim 39 wherein the arginine is present at a concentration of about 0.1 to about 0.2M.

42. A process as recited in claim 39 wherein the stabilizing agent further comprises histidine.

43. A process as recited in claim 42 wherein the histidine is present at a concentration of about 0.025M.

44. A process as recited in claim 39 wherein the stabilizing agent further comprises human serum albumin.

45. A process as recited in claim 44 wherein the human serum albumin is present at a concentration of about 0.05% (wt/vol) to about 3% (wt/vol).

46. A process as recited in claim 44 wherein the human serum albumin is present at a concentration of about 0.5% (wt/vol).

47. A process as recited in claim 39 wherein the Factor VIII complex composition has a specific-activity of at least 50 units of Factor VIII:C activity per mg of total protein.

48. A process as recited in claim 39 wherein the lyophilized Factor VIII complex composition is reconstituted at room temperature.

49. A process as recited in claim 39 wherein the reconstituted Factor VIII complex composition retains at least 80% of its original reconstituted activity after the reconstituted Factor VIII complex is incubated for about 22 days at room temperature.

* * * * *

UNITED STATES PATENT AND TRADEMARK OFFICE
CERTIFICATE OF CORRECTION

PATENT NO. : 5,399,670
DATED : March 21, 1995
INVENTOR(S) : Prabir Bhattacharya; Toshiharu Motokubota It is certified that error appears in the above-indentified patent and that said Letters Patent is hereby corrected as shown below:

Column 5, line 10, change "0,025M" to -- 0.025M --.

Column 5, line 52, change "complex/mi" to -- complex/ml --.

Column 6, lines 61,62, after "1 and 2," delete "was not and 2,".

Column 6, line 65, change "0,025M" to -- 0.025M --.

Signed and Sealed this

Twenty-sixth Day of September, 1995

Attest:

BRUCE LEHMAN

*Attesting Officer*  *Commissioner of Patents and Trademarks*